(12) United States Patent
Smith et al.

(10) Patent No.: US 10,551,311 B2
(45) Date of Patent: Feb. 4, 2020

(54) DETERMINING AN ABSORPTION OR TURBIDITY COEFFICIENT OF A LIQUID

(71) Applicants: Starna Scientific Ltd., Hainault, Essex (GB); Stephen Smith, Colchester, Essex (GB); Norman McMillan, Craiguecullen, County Carlow (IE); Martina O'Neill, Dublin, Tallaght (IE); Sven Riedel, Norderstedt (DE)

(72) Inventors: Stephen Smith, Colchester (GB); Norman McMillan, Craiguecullen (IE); Martina O'Neill, Dublin (IE); Sven Riedel, Norderstedt (DE); John Hammond, Hainault (GB)

( * ) Notice: Subject to any disclaimer, the term of this patent is extended or adjusted under 35 U.S.C. 154(b) by 83 days.

(21) Appl. No.: 15/519,166

(22) PCT Filed: Oct. 14, 2015

(86) PCT No.: PCT/EP2015/073823
§ 371 (c)(1),
(2) Date: Apr. 14, 2017

(87) PCT Pub. No.: WO2016/059131
PCT Pub. Date: Apr. 21, 2016

(65) Prior Publication Data
US 2017/0227463 A1 Aug. 10, 2017

(30) Foreign Application Priority Data
Oct. 14, 2014 (GB) .................................. 1418200.0

(51) Int. Cl.
*G01N 21/95* (2006.01)
*G01N 21/59* (2006.01)
(Continued)

(52) U.S. Cl.
CPC ........... *G01N 21/59* (2013.01); *G01N 21/314* (2013.01); *G01N 21/51* (2013.01); *G01N 21/255* (2013.01);
(Continued)

(58) Field of Classification Search
CPC ............................. G01N 21/59; G01N 21/95
See application file for complete search history.

(56) References Cited

U.S. PATENT DOCUMENTS 6,188,476 B1 * 2/2001 Hafeman ............. G01N 21/253
356/343
8,912,007 B2 * 12/2014 Bjornson .............. B01L 3/0241
436/165

(Continued)

FOREIGN PATENT DOCUMENTS

| EP | 2071317 | 6/2009 |
|---|---|---|
| GB | 2494693 | 3/2013 |

(Continued)

OTHER PUBLICATIONS

McMillan N D et al., "Quantitative drop spectroscopy using the drop analyser: theoretical and experimental approach for microvolume applications of non-turbid solutions; Quantitative drop spectroscopy using the drop analyser." Measurement Science and Technology. vol. 19, No. 5. May 1, 2008.

(Continued)

*Primary Examiner* — Rebecca C Bryant
(74) *Attorney, Agent, or Firm* — Whiteford, Taylor & Preston, LLP; Gregory M. Stone

(57) ABSTRACT

A method of determining an absorption or turbidity coefficient of a liquid involves storing a set of data describing a plurality of droplets or other discrete bodies of liquid of different shapes, sizes and absorption or turbidity coefficients. Each body is captured as a combination of a mea-
(Continued)

surable transmission parameter obtained by modelling the interaction of light with a drop, and of one or more dimensional measurements selected from lengths, areas and volumes. The absorption or turbidity coefficient is indicated also. By measuring the transmission of light through a real body of liquid, and making measurements allowing the droplet to be specified, the absorption or turbidity coefficient associated with a droplet giving rise to the same behaviour in transmitting light can be identified from the data set.

23 Claims, 5 Drawing Sheets

(51) Int. Cl.
    *G01N 21/31*     (2006.01)
    *G01N 21/51*     (2006.01)
    *G01N 21/25*     (2006.01)

(52) U.S. Cl.
    CPC ......... *G01N 21/5907* (2013.01); *G01N 21/95* (2013.01); *G01N 2201/12* (2013.01)

(56) References Cited

U.S. PATENT DOCUMENTS

| | | | |
|---|---|---|---|
| 8,947,668 B2* | 2/2015 | Hulme | G01N 21/11 356/432 |
| 2013/0293887 A1 | 11/2013 | Castiglioni | |
| 2014/0206093 A1 | 7/2014 | Bjornson et al. | |

FOREIGN PATENT DOCUMENTS

| | | |
|---|---|---|
| WO | 2007/131945 | 11/2007 |
| WO | 2012/140232 | 10/2012 |

OTHER PUBLICATIONS

Search Report issued in co-pending application No. GB1418200.0 dated Mar. 19, 2015.
Search Report issued in co-pending application No. PCT/EP2015/073823 dated Jan. 27, 2016.

* cited by examiner

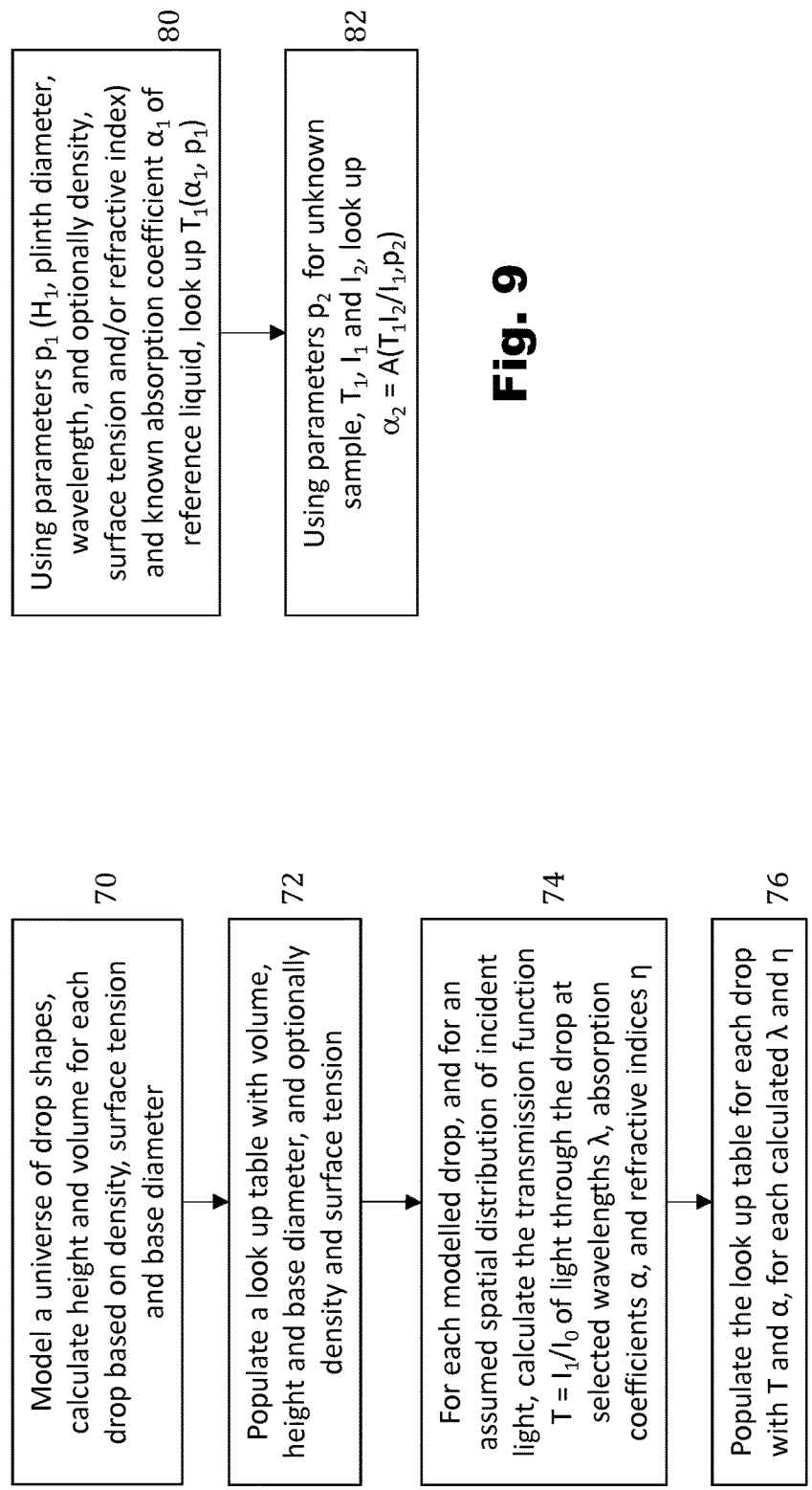

DETERMINING AN ABSORPTION OR TURBIDITY COEFFICIENT OF A LIQUID

TECHNICAL FIELD

This invention relates to the determination of absorption or turbidity coefficients of liquids.

BACKGROUND ART

The standard technique in the art for measuring an optical absorption coefficient $\alpha$ of a liquid uses an optical cell (a cuvette) in which a collimated beam of light goes through the liquid along a path of well-defined length l. The cell is filled with a reference liquid, and the light detected $I_1$ through the cell containing a reference liquid of coefficient $\alpha_1$ is measured. Then the cell is filled with the unknown liquid of unknown coefficient $\alpha_2$, and the intensity $I_2$ through the same cell is measured. The coefficient $\alpha_2$ is then obtained by the expression:

$$\alpha_2 = \alpha_1 + \{\log_e I_1 - \log_e I_2\}/l$$

This method has several drawbacks. It requires the use of collimated light and will not work accurately with non-collimated light. Furthermore, the Beer's Law equation from which the expression above derives assumes ideal conditions: it does not take account of reflections introduced by the four interface surfaces traversed by the light (air-glass followed by glass-liquid at the front glass wall of the cell, and then liquid-glass followed by glass-air at the back glass wall). Multiple reflections can occur which means that the pathlength assumption is incorrect in practice. If liquids of different refractive index are employed then the amount of light reflected at the liquid-glass interfaces changes between the reference liquid and the unknown liquid. The method also assumes that all of the absorption occurs due to the liquid and none due to the glass.

Turbidity is typically measured using a commercial turbidimeter which measures the transmission of light through a standard cuvette in similar manner and with similar drawbacks.

DISCLOSURE OF THE INVENTION

There is provided a method of determining an absorption coefficient of a liquid, comprising the steps of:
(a) storing, in a memory accessible by a processing apparatus, a set of data describing a plurality of discrete bodies of liquid of different shapes, sizes and absorption coefficients, wherein each discrete body is captured in said data set as a combination of a measurable transmission parameter and of one or more dimensional measurements selected from lengths, areas and volumes, and wherein for each such discrete body said absorption coefficient is indicated in said data set;
(b) providing said liquid in the form of a sample body of a shape and size encompassed by said data set;
(c) measuring one or more dimensional measurements of said sample body suitable to specify a discrete body in said data set or an interpolated position intermediate to a plurality of discrete bodies in said data set;
(d) measuring a transmission value for light through said sample body and determining a transmission parameter therefrom;
(e) providing said transmission parameter and said dimensional measurement(s) as inputs to a processing apparatus; and
(f) said processing apparatus determining from said data set said absorption coefficient associated with the discrete body specified by said transmission value and said dimensional measurement(s).

The aforesaid set of data may comprise either calculated or measured data, or a combination of the two. We have constructed the data set by a ray tracing procedure, as described below, but other methods, such as finite element analysis, are equally appropriate.

In contrast to the conventional cuvette technique, the method described above makes no assumption about pathlength, which is not a useful concept in this analysis. By storing a data set in which the actual transmission characteristics through numerous droplets, each having a known optical absorption coefficient and a known dimension, the real-world transmission values through a sample droplet can be cross-referenced to look up the absorption coefficient.

Preferably, said step of measuring a transmission value comprises measuring the intensity of light transmitted through said sample body, and wherein said transmission parameter is determined by normalising said measured intensity against a transmission value for a control liquid of known optical properties.

In contrast to the existing technique, in which assumptions are made about the experimental environment (standard cell size, same values for reference and test liquid, etc.), the reference measurement in this technique can be performed on a droplet of different size than the unknown sample droplet.

The method preferably further comprises the steps of:
i. providing said control liquid in the form of a reference body of a shape and size encompassed by said data set;
ii. measuring one or more dimensional measurements of said reference body suitable to specify a discrete body in said data set or an interpolated position intermediate to a plurality of discrete bodies in said data set;
iii. measuring a transmission value for light through said reference body;
iv. providing said transmission value and said dimensional measurement(s) as inputs to a processing apparatus; and
v. said processing apparatus determining from said data set, using said inputs and a predefined value for the absorption coefficient of said liquid of known optical properties, the incident light intensity giving rise to said transmission value.

This technique enables two different measurements, one through the reference liquid and the other through the sample liquid, to be used to calibrate the incident light intensity onto the sample droplet.

Preferably, the step of determining a transmission parameter in step (d) of claim 1 comprises calculating said transmission parameter as a ratio between a measured intensity of light and said incident light intensity obtained in step (v) of claim 3.

Optionally, the data set is provided as a first subset of data from which the sample body's absorption coefficient is determined and a second subset of data describing a plurality of discrete bodies of said liquid of known optical properties from which the incident light intensity is derivable for the liquid of known optical properties, wherein each discrete body is captured in said second subset of data as a combination of a measurable transmission parameter and of one or more dimensional measurements selected from lengths, areas and volumes.

Preferably, said liquid of known optical properties is a pure sample of a reference liquid.

Alternatively, said liquid of known optical properties may be the same as the sample liquid, wherein the absorption coefficient is known at a first wavelength at which an analyte in the liquid is non-absorbing, and is unknown at a second wavelength at which an analyte in the liquid absorbs light.

In this way, measurement of the transmitted light at the first wavelength allows a "blank" reading to be obtained, which is then used to calculate the incident light intensity, and that value can be used, taking into account any wavelength dependence of the response of the measuring system, to accurately translate the measured transmitted intensity measured at the second wavelength into an absorption coefficient (since we know the incident intensity, the transmitted intensity and so the transmission factor through the droplet, we can look up the data set to see what absorption coefficient, in a drop of the measured shape and size, would give rise to that transmission factor).

Preferably, the method further includes repeating steps (b) to (f) for a plurality of sample bodies of said liquid of varying sizes, and determining an average value for said absorption coefficient from repeated measurements.

Preferably, said data set is provided as an N-dimensional data set, wherein the number of fields N is 2 or more, and wherein said fields include at least:
 I. a field describing the dimensions of the droplet; and
 II. a field describing the measurable transmission parameter.

More preferably, the number of fields N is 3 or more and said fields additionally include one or more of the following:
 III. a wavelength or frequency of light used to make measurements;
 IV. a density of the liquid;
 V. a surface tension of the liquid;
 VI. a refractive index of the liquid;
 VII. where the field (I) describing the dimensions of the droplet is a linear dimension, a field describing a further dimension of the droplet.

In certain embodiments, said droplet volume is sufficiently small as to ensure that surface tension forces dominate gravitational forces, and wherein step (c) of measuring said one or more dimensional measurements comprises measuring a droplet height.

Preferably, step (b) comprises depositing the droplet on a constraining surface of known dimensions, such that the constraining surface provides a base of known dimensions for the droplet.

A free nanodrop which is not under any unusual stress situation will be spherical. Under gravity, increasing the size of the drop will cause the drop to deviate from the idealised spherical shape and take on shapes that can be modeled with enormous accuracy using standard methods using the Laplace-Young equation and various well-known numerical modeling methods.

The modeling methods described herein for sessile droplets deposited on a conventional (e.g. quartz) drophead are also applicable to the analysis of light passing through such drops or nanodrops made to sit precisely on a measuring instrument using a drophead with extreme hydrophobicity to levitate the spherical or near spherical sample precisely in the sample position aligned with the instrument's optical axis.

Surface activation can generate hydrophobic and hydrophilic regions for example, or lithography can generate micro and indeed nanostructures which can help position such freely suspended drops that can either through such surface forces sit free of the surface or could even be levitated by various well known methods to adopt a free droplet shape.

Accordingly, as an alternative to a droplet being deposited on a substrate, the droplet may be a free droplet suspended or levitated above a surface.

Preferably, step (c) of measuring said one or more dimensional measurements comprises measuring a sample body height Preferably, said dimensional measurement(s) provided as inputs in step (e) are limited to said measured height, or to a combination of said measured height and a known dimension of said constraining surface.

Indeed, provided that a liquid body's shape can be accurately modelled, and as long as the transmission of light through the body can be determined for each volume in the data set, there is no restriction on how the liquid body is formed or constrained.

Again, in such cases, step (c) of measuring said one or more dimensional measurements preferably comprises measuring a sample body height When a well is used, preferably said dimensional measurement(s) provided as inputs in step (e) are limited to said measured height, or to a combination of said measured height and one or more known dimensions of said well.

Preferably, the method further comprises performing the claimed method on a sample of a reference material, which may be a certified reference material, before and/or after performing the method on a liquid to be analysed.

The technique is preferably performed on a fully qualified and validated spectrometer system which has the required performance characteristics to assist the production of appropriate data for the complete measurement cycle. Generally accepted qualification protocols in regulated industries, e.g. pharmaceutical, may require that the performance is checked at the beginning and end of a measurement programme to ensure that the results are valid. These qualification protocols will be based on statistical evaluation of the calibration of the instrument by the use of appropriate traceable Certified Reference Materials, but may also include other physical instrument checks to demonstrate that the spectrometer is under control, and the data produced is fit for purpose.

Preferably, said absorption coefficient is expressed in said data set in terms of a metric which can be directly converted to or is derived from the absorption coefficient of the liquid sample body In one preferred variation, said absorption coefficient is expressed in said data set in terms of a concentration value for an analyte.

The method outlined here is one that in the first instance provides a quantitative measurement of some constant or physical property. There are many situations where such quantitative measurement can be used to identify a chemical, molecule or some other physical entity. The variation and control of the measurement situation for example in varying the angle of the illumination will lead to predictable variations in the light output for example and such forms of variation or magnitudes of variation might be used to qualitatively identify some entity of interest.

The use of activated substrates with well-known methods commonplace in nanoscience enables use of nanoparticles, nanorods, nanotubes and other nanostructures to produce an active surface that can with plasmonics or other well-known methods allow for a specific molecule (perhaps a cancer precursor molecule) that is important for diagnostic purposes. The system of a sessile drop, suspended nanodrop or other sample can produce a quantitative reading that is diagnostically or in some other way significant. The method can be used in concert with other technologies to deliver a new methodology of predictive measurement.

As an example, if the substrate on which the drop is deposited is an active surface which can generate plasmons that would excite e.g. a particular biological molecule, then the absorbing properties of a droplet will change depending on the concentration of the analyte species and the apparent concentration when subjected to excitation. Both situations can be modelled for a range of analyte concentrations given knowledge of the physical set-up, and then the transmitted intensity through the sample can be measured both in the presence of and absence of the plasmon excitation to derive the concentration of analyte.

Preferably, and particularly where multiple wavelengths are employed, the measurement of a transmission value preferably comprises measuring transmitted light using a spectrometer to obtain photometric measurements at a range of wavelengths.

The invention also provides a computer program product comprising instructions which when executed in a processor are effective to cause the processor to carry out the computation aspects of the method.

The invention also provides an apparatus configured to carry out the method.

There is further provided a method of determining a turbidity coefficient of a liquid, comprising the steps of:
(a) storing, in a memory accessible by a processing apparatus, a set of data describing a plurality of discrete bodies of liquid of different shapes, sizes and turbidity coefficients, wherein each discrete body is captured in said data set as a combination of a measurable transmission parameter and of one or more dimensional measurements selected from lengths, areas and volumes, and wherein for each such discrete body said turbidity coefficient is indicated in said data set;
(b) providing said liquid in the form of a sample body of a shape and size encompassed by said data set;
(c) measuring one or more dimensional measurements of said sample body suitable to specify a discrete body in said data set or an interpolated position intermediate to a plurality of discrete bodies in said data set;
(d) measuring a transmission value for light through said sample body and determining a transmission parameter therefrom;
(e) providing said transmission parameter and said dimensional measurement(s) as inputs to a processing apparatus; and
(f) said processing apparatus determining from said data set said turbidity coefficient associated with the discrete body specified by said transmission value and said dimensional measurement(s).

It will be appreciated that in this method, the optical property of interest is the turbidity coefficient rather than the absorption coefficient, but otherwise the structure of the method is identical. Except where indicated, or where it would be evident to the skilled person that it was inappropriate, all of the features above corresponding to dependent claims for the absorption method may be equally applied to the turbidity method, with the turbidity coefficient being substituted in the data set for the absorption coefficient.

Absorption in an absorbing liquid is straightforwardly modeled: a ray of initial intensity $I_0$ has its intensity over a path of length l changed to $I=I_0\exp\{-\alpha l\}$, where a is the absorption coefficient. The intensity loss over the path length l is $I_0[1-\exp\{-\alpha_T l\}]$; this quantity represents energy that is absorbed by the medium in which the ray is propagating.

The effect of turbidity is more complicated, but can be simulated as follows. Under turbid conditions, the direct ray suffers a loss of intensity over a path l similar to the loss due to absorption, so the direct intensity variation over a path l is $$I=I_0\exp\{-\alpha_T l\}$$

where $\alpha_T$ is the turbidity scattering coefficient.

However, the intensity $I_0[1-\exp\{-\alpha_T l\}]$ removed from the direct ray is not absorbed but is scattered out of the direct ray, so that it now contributes to a turbidity-generated optical energy density within the liquid drop. We assume that this energy density is in the form of isotropic radiation, which escapes from the drop at its air surface and also escapes into the drop-head. Some of the latter radiation will find its way into the exit fibre, and will be detected as indirect turbidity-scattered light in addition to the light detected by the direct rays. This is the macro-modeling situation.

As with the data set used for absorption coefficients, the set of data used in the turbidity method may comprise either calculated or measured data, or a combination of the two. A data set can be constructed using the assumptions outlined above, and as with the absorption data, a range of modelling techniques including ray tracing and finite element analysis may be used.

The models can be generated using the turbidity scattering coefficient or the model can be based on very detailed information on the scattering entities as in the case of nanoparticles fabricated to specific sizes and shapes. If such particulate entities are in a solution so as to form a nanoparticle suspension of known concentration a nanoparticle standard can be manufactured which has known electromagnetic constants (dielectric constants, permeability and also reflectivity of surfaces which can be engineered by coating technologies for example) for the solid (particulate) and liquid phases. The skilled person will have at his or her disposal several software packages offering the ability to model sessile/pendant/free drops, meniscuses, nanostructures and any physically defined structure, using assumptions that may be simplified or made more complex and realistic as the application requires.

For example, in measuring the turbidity of drinking water (perhaps the most widespread and commercially important application), the modelling may make assumptions as to the typical properties (e.g. reflectivity or albedo, absorptivity, shape) and size distributions of contaminant particles, and may make assumptions as to testing temperatures, leading to a relatively simplified modelling of ray paths when compared to a data set that must account for a wider range of possible contaminant properties and types.

The same method as described previously can then be used and measurements of inputs and outputs will enable the turbidity constant to be obtained for the macromodeling given the assumption of uniform particulate distribution (homogeneous $\alpha_T$ for the sample) in an exactly analogous way to the example given for a solution with a uniformly absorbing solution. Turbid solutions are ones that frequently settle and are not homogeneous and sample preparation for measurement for such non-isotropic samples are well known.

The modeling of nanoparticles and such samples with finite element analysis approaches extends the analytical capability of the method and the technique can be extended to determine the turbidity coefficient $\alpha_T$ for differently modelled solutions for example having the same nanoparticle but dispersed in liquids of different refractive index. Such a physically well-defined situation can be modeled and enables one to measure refractive index from a drop turbimeter using a suspension of known concentration of e.g. gold nanoparticles.

The modelling method described earlier is one that can be simply modified with the term $I=I_0\exp\{-\alpha_T l\}$ replacing the absorption coefficient term and the energy loss $I_0[1-\exp\{-\alpha_T l\}]$ included as a contribution to an isotropic uniform illumination.

Apart from this latter term, nothing else needs to be changed. The underlying approach to determination of turbidity and absorption are equivalent.

There will be certain situations where restrictions on the range of sample properties of the absorbing species and the scattering species would enable a measurement of both the absorption and scattering coefficients. The skilled person would be able to arrive at such restrictive and physically well-defined physical arrangements that would allow for such a dual measurement.

One particularly useful approach is to perform measurements at two wavelengths, one of which is not absorbed by the liquid medium and the other of which is. For the non-absorbed wavelength, pure turbidity data set models can be developed and measurements made at this wavelength will b used to reveal turbidity constants. For the absorbed wavelength, the data set can model the droplet to include both absorption and turbidity or, if the wavelength is extinguished far more by absorption than it is influenced by turbidity, then the turbidity can be treated as negligible and a pure absorption model can be used to determine absorption coefficients.

BRIEF DESCRIPTION OF THE DRAWINGS

FIG. 8 is a flowchart of a method for constructing data sets for use in the present methods;
and
FIG. 9 is a flowchart of the use of the data sets to obtain absorption coefficient.

DETAILED DESCRIPTION OF PREFERRED EMBODIMENTS

Figure 1:
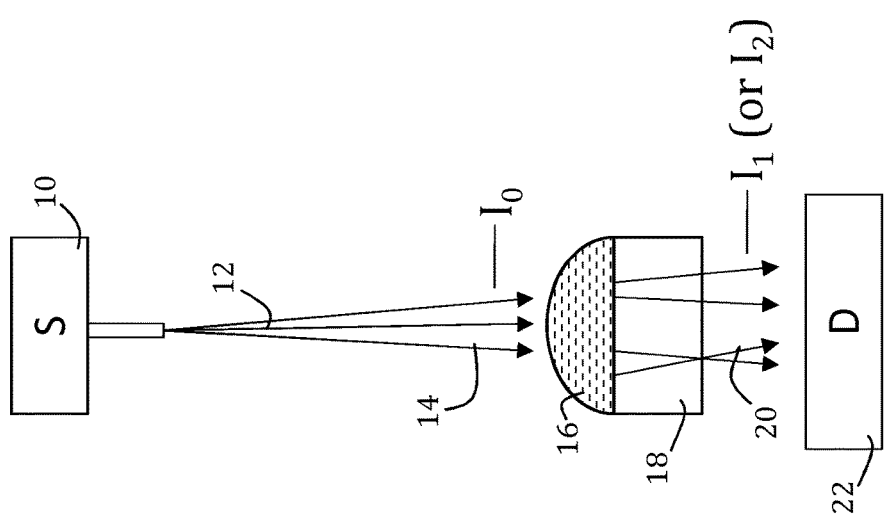
FIG. 1 is an illustration of a system for measuring optical properties of a liquid sample.

In FIG. 1 there is illustrated an optical system comprising a source 10 of light coupled to a source fibre 12 from which uncollimated light 14 issues of intensity $I_0$. The light is received by a drop 16 of liquid which sits on a quartz plinth 18, such that a portion of the light is absorbed, dispersed or reflected, and a portion 20 of intensity $I_1$ is collected at a detector 22. The detector 22 may be a CCD camera spectrometer system which allows for photometric measurements of light at different wavelengths.

The system of FIG. 1 is typically embodied in an instrument allowing easy loading of drops onto the plinth, and easy cleaning of the plinth. An example of such an instrument is described in WO 2012/140232, which is incorporated herein by reference. That system also includes environmental controls, such that after loading on the plinth the drop is enclosed within a small-volume closed environment in which there is a well of solvent which saturates the atmosphere with vapour to prevent evaporation of the drop (and changes of volume during measurement). Temperature control is obviously also important in practice, and the skilled person will be aware of the need to control environmental factors.

If the drop size changes, then there will be a different transmission of light, resulting in a change in $I_1$. Similarly, if the composition of the liquid changes, such as if a liquid of different absorption coefficient is used, then the intensity $I_1$ will also change. Furthermore if the wavelength of the light changes, this will result in a change in detected intensity $I_1$.

It is possible to model the transmission characteristics of the system for a given wavelength, drop shape and volume, absorption coefficient, and spatial distribution of incident light. By assuming an appropriate form for the spatial distribution of incident light one can model many such droplets and build up a data set for different drop shapes and volumes in respect of a range of absorption coefficients and wavelengths. This data set is simplified if one works at a single wavelength. At multiple wavelengths, one also needs to take account of the spatial distribution of light at each wavelength, if the spatial distribution is different for different wavelengths, as it may be for light coming from an optic fiber.

It should be noted that while the described system operates on the basis of modelling the droplets and the interaction of the droplets with light, one could construct the data set by experimentally determining the interaction of light with different droplets, and one could also experimentally determine the shape of a given volume of liquid, though this is less preferred due to the amount of work involved and the higher probability of error being introduced.

In the case of a droplet on a circular plinth, the diameter of the drop base is assumed to be equal to that of the plinth. This simplifies the calculation of the shape that a given volume of a particular liquid will assume. For very small diameters, the surface tension force will dominate the gravitational force and the droplet will assume a spherical section, while for larger diameters, the gravitational force will have an effect that will result in a more complex shape but still one which can be calculated and modelled. The same principles can also be applied to other well-defined liquid volumes, such as a liquid volume in a well where there is a meniscus surface at the interface with the air and the remaining surface shapes are defined by the walls of the well.

Accordingly, the system of FIG. 1 is modelled for a range of liquids and drop sizes and shapes, using ray tracing techniques such that for each modelled drop, the transmission coefficient T for the propagation of the incident light is calculated. The transmission coefficient will depend on the absorption coefficient α of the liquid, and may also depend on other parameters (e.g. volume V or height H of the drop, wavelength λ of the light). We write this functional dependence as $$T=T(\alpha,p)$$

where the symbol p denotes these additional parameters.

The intensity of light detected after passing through the reference medium is $$I_1 = kI_0 T(\alpha_1, p_1)$$

where k is a factor that represents the sensitivity of the detector, and includes equipment-dependent factors that are independent of the liquid under test. This factor need not be known, but is assumed to stay constant throughout the measurements. The parameters $\alpha_1$ and $p_1$ must be known or, if not, they must be able to be determined by additional measurements (e.g. by measuring the height of the liquid drop for a simple drop shape or measuring additional dimensions for more complex shapes).

The intensity of light detected after passing through the test medium is $$I_2 = kI_0 T(\alpha_2, p_2)$$

where $\alpha_2$ is the absorption coefficient of the test liquid, whose value is to be determined, and $p_2$ represents the other parameters which must be known or determinable.

Taking the ratio eliminates the unknowns $I_0$ and k:

$$I_2 T(\alpha_1, p_1) = I_1 T(\alpha_2, p_2)$$

Thus, $\alpha_2$ has the unique value that satisfies this equation.

In order to solve this implicit equation for $\alpha_2$, the method involves preparing a function $$A(T, p)$$

which calculates the absorption coefficient $\alpha = A(T, p)$, given the transmission coefficient T and remaining parameters p. In a sense, $A(T,p)$ is the function inverse to $T(\alpha, p)$. It is always possible to compute this function uniquely because there must be a one-to-one correspondence between T and $\alpha$. Thus, the result of the method is a determination of the unknown absorption coefficient $$\alpha_2 = A(T_1 I_2 / I_1, p_2) \text{ with } T_1 = T(\alpha_1, p_1).$$

In order to implement this method the functions $T(\alpha, p)$ and $A(T, p)$ are pre-computed. In particular, given the range of parameters p which are likely to be encountered, the corresponding drop shapes are computed, then using standard physical principles for ray tracing the transmission functions T for each such drop are computed, for a range of different absorption coefficients $\alpha$. The absorption coefficient function A is similarly calculated.

As a result, a look-up table can be constructed, according to which the transmission function $T_1 = T(\alpha_1, p_1)$ can be found for a reference droplet having the parameters $p_1$ and known absorption coefficient $\alpha_1$, and then the unknown absorption coefficient $\alpha_2 = A(T_1 I_2 / I_1, p_2)$ can be looked up for a test droplet having the parameters $p_2$, measured with the same apparatus.

Crucially, this method does not depend on the concept of a defined pathlength, and the method can take into account the possibility that the parameters will vary between one droplet and the next. There are no assumptions that an ideal test cell is being used, or that the light is following an ideal path. Internal reflections within the droplet and from the surface of the droplet are taken into account during modelling.

Experimental factors which are common to the reference and test measurements such as detector efficiency, absorption by the plinth, stray light etc. are cancelled out in the above mathematical treatment, so that the ratio of the measured intensity from the reference and test liquids, combined with accurately determinable parameters of the drop shape and wavelength, allow a complete determination of the absorption coefficient.

In contrast, prior art methods employing a standard cell or cuvette are based on simplifying assumptions which do not hold true in practice, i.e. that the light path is unique, that there are no Fresnel reflections, that there are no dimensional errors or angular errors in opposed cuvette faces, that there are no positional errors in placing the cuvette in the holder, and so on.

Furthermore, the modelling is done using uncollimated light, as are the measurements, so that unlike prior art methods, this technique can be performed without any collimated light being required. However, the form of the spatial intensity distribution of the incident light must be known.

If the attenuation of light arises primarily from turbidity, then the turbidity coefficient can be obtained in similar manner, with the difference that the modelling should take into account the difference in physical behaviour between a turbid liquid and an absorbing but non-turbid liquid. Turbidity coefficients can then be stored and looked up instead of absorption coefficients, but using similar techniques.

Modelling

A proof-of-principle database was created as follows (a complete database would be much more extensive but would follow the same principles).

1. A series of drop shapes were considered. The drops were assumed to have a circular base whose diameter ranged from 1.8 mm to 2.2 mm in increments of 0.1 mm (i.e. five different drop bases were considered). There were 10 values for the size of the drops, chosen so that the volume ranged from 1 to 4 µl; the height H and volume V was recorded for each of these 50 different drops.
2. Then a range of liquids needs to be considered; it is sufficient for the proof-of-principle to use a single liquid—water. The transmission depends on wavelength, and we considered water at 8 different wavelengths in the range 200-800 nm.
3. The water is assumed to contain dissolved absorbing material; we have modelled the absorption coefficient for 5 values in the range 0-20 $cm^{-1}$.
4. Thus, a total of 50 drop shapes needed to be modelled, with 40 values of the optical parameters for each drop. The optical transmission was modelled using a ray tracing procedure that follows the path of at least $5 \times 10^7$ rays.
5. A database was populated with the results. The database was a 5-dimensional database specifying a drop's characteristics: drop height H, base diameter D, wavelength $\lambda$, transmission coefficient T and absorption coefficient $\alpha$. Drop Volume V may be used alternatively in place of drop height H, as it will be appreciated that for a single static drop of water with a known base diameter the drop height may be used to uniquely index a given drop volume. Using drop height is preferred as the error in a length measurement compared to a volume is smaller (typically a volume measurement will give 3 times the percentage error of a height measurement).
6. Two interpolation procedures were then implemented:
   a. inputting for a reference drop the following parameters as $p_1$: $H_1$, $D_1$, $\lambda_1$, together with the known absorption coefficient $\alpha_1$, thereby allowing lookup of the interpolated transmission coefficient $T_1 = T(\alpha_1, p_1)$ for the reference drop; and
   b. inputting for a test drop measured on the same system the parameter set $p_2$ for the test drop, along with the measured ratio of intensities $I_2/I_1$ and the transmission function calculated for the reference liquid $T_1$ to give as an output the interpolated absorption coefficient function $\alpha_2=A(T_1 I_2/I_1, p_2)$.

Figure 2:
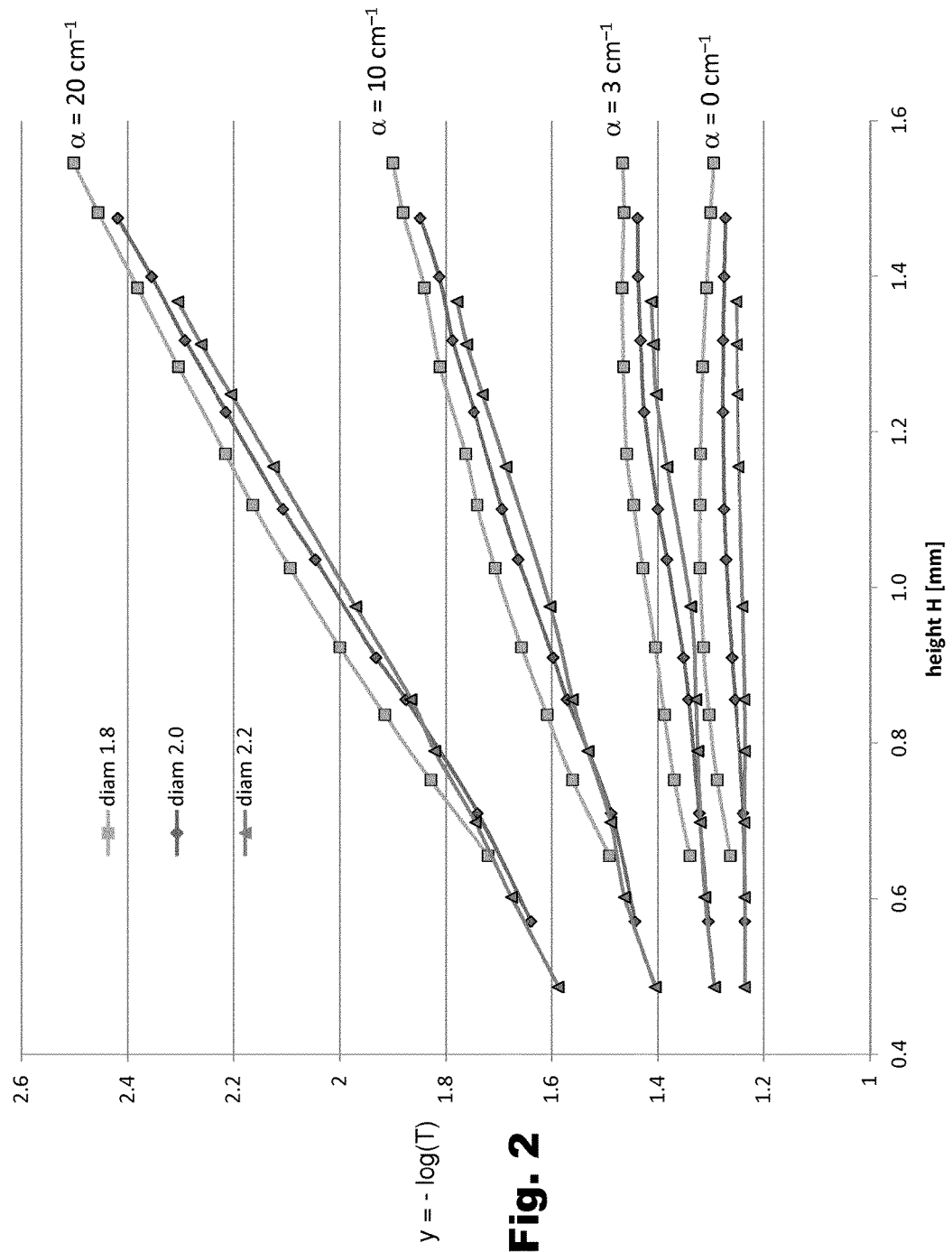
FIG. 2 is a graph of the negative of the log of the transmission factor T of light through modelled drops against drop height, for different absorption coefficients.

FIG. 2 shows how the quantity $y=-\log_{10}(T)$ depends on height H for various values of $\alpha$ and D. From this it can be seen that measurement of height allows an accurate determination of the transmission value T for a given value of base diameter and absorption coefficient.

Height Measurement

In use free-standing drops are characterised by parameters including base diameter and height which allow the drop shape to be specified. The base diameter is fixed, for a drop on a circular plinth, by the diameter of the plinth, and for a given liquid the height is thus determinative of the drop shape. Height can be measured far more accurately than volume. For example, using the confocal light pen method below, resolutions of 0.016% in height can be obtained as compared with 0.5% volume resolution with a pipette.

The preferred measurement is using a chromatic confocal light pen, such as the Endo light pen and TopSens controller sold by Polytec GmbH of Waldbronn, Germany. The sensor projects polychromatic light (white light) to the target surface. The sensor lenses are designed to use controlled chromatic aberration to focus each light wavelength at a specific distance. In reverse, the sensor will then receive the light that is reflected from the target surface and transfer it to the controller. This is followed by the spectral analysis, and then the data stored in the controller are used to calculate the distances. The primary use of this is to measure distance to the top of the plinth on which the droplet is to be deposited, and then measure the distance to the top of the droplet after it has been deposited, thereby giving a very accurate measurement of droplet height.

The invention is not limited to measuring height in this way. One can also measure the height using micro cameras, optical verniers, or interferometers, to give three alternative examples. One could also, instead of measuring drop height, measure drop volume using an accurate system such as a high resolution camera to determine the dimensions and shape of the drop surface and fit this to a model of the universe of possible drops.

Measurement of Refractive Index

It is to be noted again that while this system is primarily described in terms of drops with a circular base, preferably obtained by depositing the drop on a plinth or other circular surface which is wetted by the drop and thus defines the drop base diameter, the use of such a plinth is not required, and nor is it required that the measurement be done on a drop. A drop deposited in a well having a well-defined shape will take up a shape which is determined entirely by the drop height, once the surface tension and density of the liquid are known, and the methods outlined here are equally applicable to such bodies of liquid, which can be modelled both in terms of their shape and size and in terms of the transmission of incident light through the drop for a given absorption coefficient.

Figure 5:
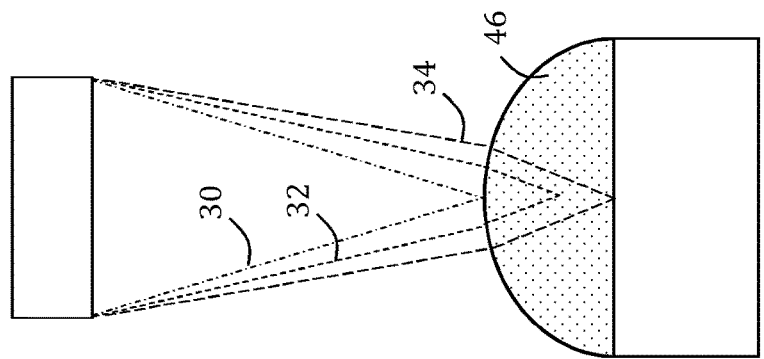
FIG. 5 is a ray diagram of the FIG. 4 system when a drop is deposited.
Figure 4:
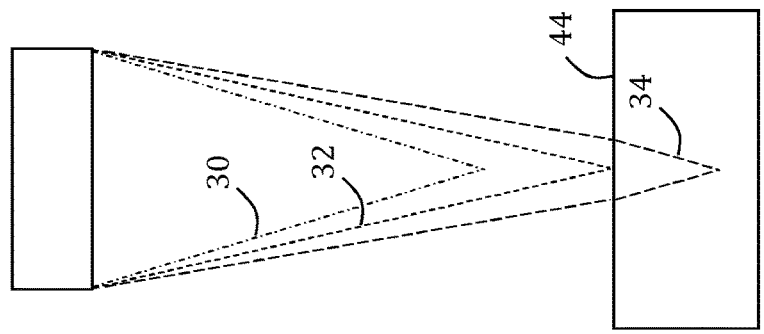
FIG. 4 is a ray diagram of the FIG. 3 system when a plinth is introduced.
Figure 3:
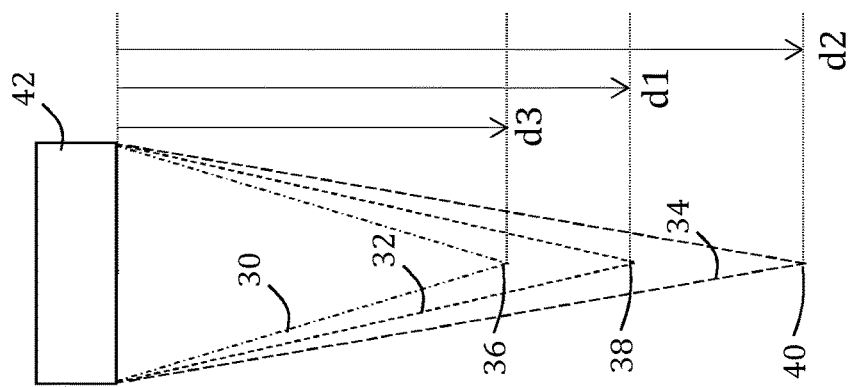
FIG. 3 is a ray diagram of a confocal light pen system.

Referring to FIGS. 3-5, the confocal pen can also be used to determine refractive index in a drop. As previously noted, the sensor lenses focus each light wavelength at a specific distance. In FIG. 3, this is shown in an exaggerated fashion with three wavelengths 30, 32, 34 focussed at three different focal points 36, 38, 40 from a confocal pen 42. If reflective surfaces were placed at points 36, 38 and 40, the confocal pen system software would (following spectrographic analysis that determined a peak in returned light at the respective wavelengths 30, 32, 34) record reflective surfaces at distances d3, d1 and d2, respectively according to its calibration for the unrefracted light cone in air. While only three ray paths are shown the system is actually polychromatic and may have a distance resolution of the order of 0.005 µm over a measuring range of 0.12 mm.

As shown in FIG. 4, if a plinth is positioned with its surface at point 38, this will appear as a reflection from the wavelength 32, recorded at a distance d1. There is no reflection at wavelength 30 focussed above the plinth surface, and none at wavelength 34 which is refracted inside the plinth volume to a new focal point 40a. Thus, the software will indicate a distance d1 to a reflective surface 44.

Then as shown in FIG. 5, when a drop 46 is placed on the plinth, two reflections are measured. A first reflection occurs at wavelength 30 and is therefore interpreted (correctly) as a reflection in air at distance d3. It can be seen that the wavelength 32, which had previously focussed at the plinth surface 44 is now refracted by the liquid 46 to a focal point within the liquid body and does not reflect strongly. However, the wavelength 34, also refracted by the liquid drop 46, is now focussed on the plinth surface 44 and so a strong reflection is detected at wavelength 34.

In practice, the software used for confocal light pens will be configured to report a reflection from a particular wavelength as a distance. If no adjustment is made for the presence of the liquid, the software will assume both reflections are made in air, and will report the presence of surfaces at distances d3 and d2, as it has no way of knowing that the third wavelength 34 is actually being refracted to focus at a distance d1. As far as the software is concerned, therefore, the plinth, due to its being reflected by (say) orange light at wavelength 34 rather than (say) green light at wavelength 32, has shifted from distance d1 to distance d2. That shift in distance is illusory and instead is due to refraction of a particular wavelength by the drop to reflect on the surface 44. We can view this shift in reflected wavelengths as a change of distance X to the top of the plinth where X=d2−d1. (Incidentally, while the original reflection at the original wavelength has shifted upwards within the drop, just as one would expect from basic physics experiments on refractive index, the confocal software sees a reflection at a different wavelength, which it associates (in air) with more distant surfaces, and so it provides a result that appears to show that the addition of the drop makes the apparent distance to the plinth surface increase, not decrease.)

Figure 6:
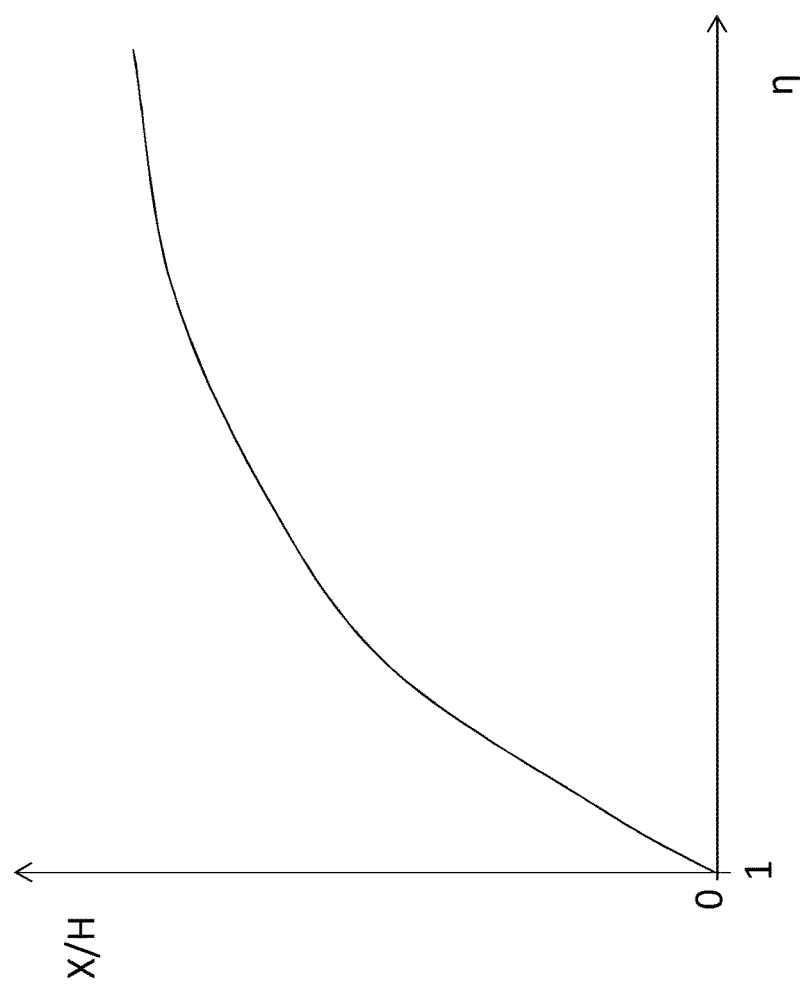
FIG. 6 is a graph of distance measurements from the confocal system versus refractive index.

Referring to FIG. 6, it can be seen that a calibration graph can be created to describe the relationship between this apparent distance shift X divided by drop height H, when graphed against refractive index η. From such a graph, the refractive index can be derived immediately from the three distances measured by the confocal light pen, namely distance to plinth without drop, d1; distance to plinth with drop, d2; and distance to top of drop d3, since X/H=(d2−d1)/(d1−d3).

The refractive index can also be measured in other ways, such as with an Abbe refractometer, or can be looked up for known liquids. Typically, one will make several measurements and calculate an average and standard deviation for the refractive index.

If the liquid is to be investigated not just for refractive index but also dispersion then the colour of light incident on the plinth can be selected. The measurement then would be specifically for the wavelength selected. The refractive index graph versus wavelength is a classically known linear relationship for most liquids and a graph of refractive index versus wavelength can give the dispersion.

Alternatively, if one measures refractive index at a known wavelength the dispersion can usually be projected from a theoretical relationship because of the knowledge of the dispersion slope.

A system is set up as in FIG. 1 with a quartz cylindrical plinth, a suitable source emitting light from a fibre with a diverging conical beam with a known angular spread above the top of the plinth. A detector is positioned under the plinth. Using this system, the output from the detector can be measured as a power value corresponding to the detected light intensity at the underside of the plinth.

A confocal light pen as described earlier (not shown in FIG. 1) is also provided which can be moved into place for each drop to measure its height with an accuracy of 0.016%. Thus for each drop, the system is able to measure height H, refractive index $\eta$, and detected light intensity I.

Figure 7:
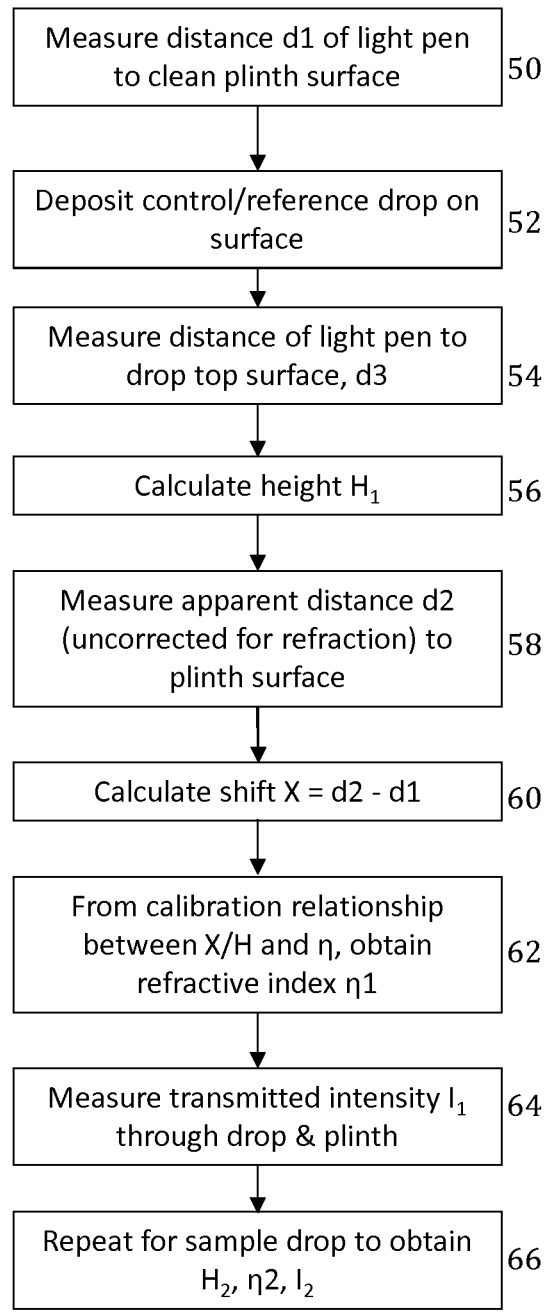
FIG. 7 is a flowchart of a measurement protocol.

The measurement protocol is illustrated in the flowchart of FIG. 7. In step 50, the distance d1 of the light pen to the clean plinth surface is measured. Then, step 52, a control or reference drop is deposited on the plinth surface, ensuring that the volume is sufficient to spread across to the plinth edge and insufficient to overflow the plinth. It is not necessary to accurately measure the drop volume with a pipette, but a pipette or dropper can conveniently be used to deposit an approximate known volume e.g. 2 microliter.

Then, step 54, we measure the distance of the light pen to the drop top surface, d3, and from this, step 56, we calculate the drop height H1. If the refractive index of the reference liquid is not accurately known, or if we want to verify and ensure a well calibrated system, we measure, step 58, the apparent distance d2 reported by the confocal pen system (uncorrected for refraction) to the plinth surface. From this, step 60, we can calculate the apparent shift in the plinth position X=d2−d1.

Referring to a calibration graph such as FIG. 6, or to a stored look-up table capturing the same relationship, or to an equation describing the shape of the calibration graph in FIG. 6, we obtain, step 62, the refractive index $\eta_1$.

We then measure, step 64 the transmitted intensity of light $I_1$ through the reference drop and plinth.

This procedure is then repeated, step 66, such that using a sample drop having an unknown concentration of analyte and thus an unknown absorption coefficient, we repeat each of the steps 50 to 64 $H_2$, $\eta_2$, $I_2$ for the sample liquid.

The steps employed in setting up the software are illustrated in the flowchart of FIG. 8. In step 70 we model a universe of drop shapes, calculate the height and volume for each drop based on density, surface tension and base diameter. The parameters of density, surface tension and base diameter can be varied if the system is to be used with different values for these parameters, or can be assumed to be fixed, giving a smaller universe of modelled drops more suited to a limited range of applications, at the choice of the system designer.

In step 72, we populate a look up table (such as the table for which an extract has been illustrated below in Table 1) with volume, height and base diameter, and optionally density and surface tension. It should be noted that volume and height are alternatives and the table need only record e.g. the height, for well behaved, static drops having a circular base and known density and surface tension.

For each modelled drop we not only have the above mentioned parameters, but the modelling also gives a complete description of drop surface shape. Using this, we model the transmission of light through the drop, step 74. For an assumed spatial distribution of incident light, appropriate software, which can be ray tracing software, is used to model the transmission of light through the drop and plinth, giving a value for the transmission coefficient $T=I_1/I_0$ at selected wavelengths $\lambda$, absorption coefficients $\alpha$, and refractive indices $\eta$. Again, in a simplified data set the refractive index might be assumed at a single value. One can also build a specific look-up table for the reference liquid with a single absorption coefficient assumed.

Instead of ray tracing, alternative modelling techniques can be used. For example, electromagnetic modelling software using finite element analysis, such as COMSOL Multiphysics from Comsol AB of Sweden, might be used. One could even build the table using real drops and real measured transmission factors, though this would be unduly laborious for most applications.

In step 76, we populate the look up table for each drop with T and a, for each calculated $\lambda$ and $\eta$. Other parameters such as temperature can be used to give an even more complex model, or alternatively an assumption can be made about working at a standard temperature (e.g. 20° C.) and all values can be calculated for that temperature and measurements made at that temperature.

The following table shows a typical partial extract from the database, showing the 5-dimensional dataset (V or H, T, $\alpha$, $\lambda$ and D), in respect of six drops with the same base diameter of 1.8 mm:

TABLE 1

| V | H | T | α | λ | D |
| --- | --- | --- | --- | --- | --- |
| 0.98747 | 0.65558 | 0.054474 | 0 | 200 | 1.8 |
| 1.1888 | 0.75226 | 0.051428 | 0 | 200 | 1.8 |
| 1.3825 | 0.8362 | 0.049651 | 0 | 200 | 1.8 |
| 1.6037 | 0.92295 | 0.048429 | 0 | 200 | 1.8 |
| 1.8931 | 1.0246 | 0.047763 | 0 | 200 | 1.8 |
| 2.1507 | 1.1058 | 0.047679 | 0 | 200 | 1.8 |

It will be appreciated that there are two database lookups, and these can be performed using a single database or using different databases.

For the first lookup, a control or reference liquid of known absorption coefficient is involved, and the database simply needs to provide the transmission coefficient for drops of different sizes (height/volume) at the wavelength being used for the control measurement and for the incident light distribution at that wavelength (the distribution from an optic fiber, for instance, may change with wavelength, and so the modelled data should take this into account). That transmission coefficient $T_1$, along with the measured intensity of light transmitted through the control liquid body, will provide a value for the incident light intensity $I_0$ via the relation $I_1=T_1 \cdot I_0$.

For the second lookup, the absorption coefficient is not known and the lookup needs to find that parameter. The transmission parameter $T_2$ used as an input is the measured (transmitted) intensity of light through the reference droplet $I_2$, divided by the incident intensity (given by $I_1/T_1$). Using this transmission parameter, the drop volume/height, and so on, the data set used for the second lookup includes a value for the absorption coefficient.

In the case that turbidity coefficient is to be measured, the turbidity coefficient, $\alpha_T$, will be stored instead of the absorption coefficient, and in the remaining description it is to be understood that the two are interchangeable in the alternative methods to determine one or other of the coefficients.

FIG. 9 shows how the data set or look-up table is used in practice, with reference to the previously described protocol for taking measurements, as seen in FIG. 7.

In step 80, Using parameters p1 (which include height H1, plinth diameter d, wavelength λ, and optionally density ρ, surface tension a and/or refractive index η) and known absorption coefficient $\alpha_1$ of reference liquid, we look up $T_1(\alpha_1, p1)$. This tells us what proportion T of incident light with a known spatial distribution will emerge from the drop to be measured as $I_1$. In turn this means that the incident light intensity $I_0 = I_1/T_1$.

In step 82, a similar set of measurements are taken for the unknown sample drop, i.e. providing a corresponding set of parameters $p_2$, and these are then used to identify the absorption coefficient of the liquid. To do so, we need to identify the correct entry in the table according to the (not directly known) transmission parameter for the drop. However, we do know the transmitted light intensity $I_2$ and we know that the transmission parameter $T_2 = I_2/I_0$ and therefore $T_2 = T_1 I_2/I_1$, so this value is used for T2 to identify the correct entry in the table and look up the absorption coefficient which had been used in the modelling step to give rise to that transmission parameter for the identified set of parameters p2.

It should be appreciated that the value retrieved, i.e. absorption coefficient, can be presented as a concentration value for a particular analyte of interest, e.g. for DNA or for proteins.

While the measurement steps described above assume that the same wavelength is used for both the sample and reference liquids, this is not essential. Also while the reference liquid is assumed to be different to the sample, this is also not essential.

A variation of the same method relies on the fact that many samples will have an unknown concentration of an analyte (such as DNA or protein) in a known liquid carrier, such as water. Water and DNA (or protein) have non-overlapping absorption bands. Thus, at a wavelength of 977 nm there is a very well-defined absorption peak for water and no absorbance by DNA. At a wavelength of 260 nm, water has no absorbance while DNA has a well-defined absorption peak.

Therefore, a sample drop of water containing an unknown amount of DNA can be placed on the plinth (or in the microwell etc.) and the transmission of light through the sample at 977 nm will be the same as if a "blank" drop of water were being measured. As with the reference drop above, the data set can be consulted, for 977 nm transmission through water droplets, to determine the incident light intensity.

The system must be pre-calibrated so that there is a known relationship between the source output intensity and spatial distribution of light at 977 nm and the source output intensity and spatial distribution of light at 260 nm. This additional factor is then used to adjust the baseline intensity for the 260 nm measurement so that instead of $I_0 = I_1/T_1$, we have $I_{0(260)} = k \cdot I_{0(977)} = k(I_{1(977)}/T_{1(977)})$, where k is a correction or calibration factor taking account of the change of response of the system (including both source intensity change and change in the detector response) from 977 to 260 nm. We can then substitute this into the step 82 lookup to obtain the absorption coefficient at 260 nm (or if preferred, a lookup of the concentration of DNA).

The method outlined herein represents a direct theoretical prediction/mapping of the measurement (absorption here but more frequently this will be concentration for the analysts which is obtained from a direct correspondence of the one to the second quantity) from a knowledge of the measurement conditions of the drop under test and the measurand error (photometric transmission taken in two steps with the control liquid and the sample).

The method removes an established intermediate calibration step of previous spectroscopic methods based on the Beer-Lambert law that is done with either graphical or complex statistical computations, but either way involves additional calibration measurements of aliquots and handling error propagation estimates and associated error calculations.

More particularly, in traditional methods, a calibration graph is prepared for a series of aliquots of known concentration and the absorbance through each aliquot, using a standard cuvette, is measured. This gives a calibration graph with a line indicating absorbance plotted against concentration, having an error band on either side of the line. Then in making absorbance measurements for an unknown sample, the absorbance values (typically ten are taken, averaged and a standard deviation calculated) are mapped to concentrations by plotting the measured absorbance, plus or minus an error (typically 3.6 times the standard deviation) against the error band, where the error propagates to give a wider error in measured concentration.

The advantage of the new procedure is that a series of measurements will again produce an average and a standard deviation. However, this measurement error will not propagate if it can be compared against a set of measurements made on standard solutions with tightly controlled concentrations and standard deviations.

The invention claimed is:

1. A method of determining at least one of an absorption coefficient and a turbidity coefficient of a liquid, comprising the steps of:
   (a) storing, in a memory accessible by a processing apparatus, a set of data describing a plurality of discrete bodies of liquid of different shapes, sizes and at least one of absorption coefficients and turbidity coefficients, wherein each discrete body is captured in said data set as a combination of a measurable transmission parameter and of one or more dimensional measurements selected from lengths, areas and volumes, and wherein for each such discrete body at least one of said absorption coefficient and said turbidity coefficient is indicated in said data set;
   (b) providing said liquid in the form of a sample body of a shape and size encompassed by said data set;
   (c) measuring one or more dimensional measurement(s) of said sample body selected from the group consisting of a length measurement of the sample body, an area measurement of the sample body and a volume measurement of the sample body, where said length measurement, said area measurement and said volume measurement exclude optical path length, suitable to specify a discrete body in said data set or an interpolated position intermediate to a plurality of discrete bodies in said data set;
   (d) measuring a transmission value for light through said sample body and determining a transmission parameter therefrom;
   (e) providing said transmission parameter and said dimensional measurement(s) as inputs to a processing apparatus; and
   (f) said processing apparatus determining from said data set at least one of said absorption coefficient and said turbidity coefficient associated with the discrete body specified by said transmission value and said dimensional measurement(s).

2. The method of claim 1, wherein said step of measuring a transmission value comprises measuring the intensity of light transmitted through said sample body, and wherein said transmission parameter is determined by normalizing said measured intensity against a transmission value for a control liquid of known optical properties.

3. The method of claim 2, further comprising the steps of:
i) providing said control liquid in the form of a reference body of a shape and size encompassed by said data set;
ii) measuring one or more dimensional measurements of said reference body suitable to specify a discrete body in said data set or an interpolated position intermediate to a plurality of discrete bodies in said data set;
iii) measuring a transmission value for light through said reference body;
iv) providing said transmission value and said dimensional measurement(s) as inputs to a processing apparatus; and
v) said processing apparatus determining from said data set, using said inputs and a predefined value for the absorption coefficient or turbidity coefficient of said liquid of known optical properties, the incident light intensity giving rise to said transmission value.

4. The method of claim 3, wherein said step of determining a transmission parameter in step (d) of claim 1 comprises calculating said transmission parameter as a ratio between a measured intensity of light and said incident light intensity obtained in step (v) of claim 3.

5. The method of claim 3, wherein said data set is provided as a first subset of data from which the sample body's absorption coefficient or turbidity coefficient is determined and a second subset of data describing a plurality of discrete bodies of said liquid of known optical properties from which the incident light intensity is derivable for the liquid of known optical properties, wherein each discrete body is captured in said second subset of data as a combination of a measurable transmission parameter and of one or more dimensional measurements selected from lengths, areas and volumes.

6. The method of claim 2 wherein said liquid of known optical properties is a sample of a reference liquid having a purity greater than a predetermined threshold.

7. The method of claim 2, wherein said method further comprises a method of determining said absorption coefficient, and wherein said liquid of known optical properties is the same as the sample liquid, wherein the absorption coefficient is known at a first wavelength at which an analyte in the liquid is non-absorbing, and is unknown at a second wavelength at which an analyte in the liquid absorbs light.

8. The method of claim 1, further comprising repeating steps (b) to (f) for a plurality of sample bodies of said liquid of varying sizes, and determining an average value for said absorption coefficient or turbidity coefficient from repeated measurements.

9. The method of claim 1, wherein said data set is provided as an N-dimensional data set, wherein the number of fields N is 2 or more, and wherein said fields include at least:
I) a field describing the dimensions of the discrete body; and
II) a field describing the measurable transmission parameter.

10. The method of claim 9, wherein the number of fields N is 3 or more and said fields additionally include one or more of the following:
III) a wavelength or frequency of light used to make measurements;
IV) a density of the liquid;
V) a surface tension of the liquid;
VI) a refractive index of the liquid;
VII) where the field (I) describing the dimensions of the discrete body is a linear dimension, a field describing a further dimension of the discrete body.

11. The method of claim 1, wherein said sample body volume is sufficiently small as to ensure that surface tension forces dominate gravitational forces, and wherein step (c) of measuring said one or more dimensional measurements comprises measuring a sample body height.

12. The method of claim 1, wherein step (b) comprises depositing the sample body as a droplet on a constraining surface of known dimensions, such that the constraining surface provides a base of known dimensions for the droplet.

13. The method of claim 12, wherein step (c) of measuring said one or more dimensional measurements comprises measuring a sample body height.

14. The method of claim 11, wherein said dimensional measurement(s) provided as inputs in step (e) are limited to said measured height, or to a combination of said measured height and a known dimension of said constraining surface.

15. The method of claim 1, wherein step (b) comprises depositing the sample body in a well of known dimensions.

16. The method of claim 15, wherein step (c) of measuring said one or more dimensional measurements comprises measuring a sample body height.

17. The method of claim 16, wherein said dimensional measurement(s) provided as inputs in step (e) are limited to said measured height, or to a combination of said measured height and one or more known dimensions of said well.

18. The method of claim 1, further comprising performing the method of claim 1 on a sample of a reference material, which may be a certified reference material, before and/or after performing the method on a liquid to be analyzed.

19. The method of claim 1, wherein said absorption coefficient or turbidity coefficient is expressed in said data set in terms of a metric which can be directly converted to or is derived from the absorption coefficient or turbidity coefficient respectively of the liquid sample body.

20. The method of claim 19, wherein said absorption coefficient or turbidity coefficient is expressed in said data set in terms of a concentration value for an analyte.

21. The method of claim 1, wherein the measurement of a transmission value comprises measuring transmitted light using a spectrometer to obtain photometric measurements at a range of wavelengths.

22. A computer program product comprising instructions which when executed in a processor are effective to cause the processor to determine an optical property selected from an absorption coefficient and a turbidity coefficient by:
a) storing, in a memory accessible by said processing apparatus, a pointer to a set of data describing a plurality of discrete bodies of liquid of different shapes, sizes and absorption or turbidity coefficients, wherein each discrete body is captured in said data set as a combination of a measurable transmission parameter and of one or more dimensional measurements selected from lengths, areas and volumes, and wherein for each such discrete body said absorption or turbidity coefficient is indicated in said data set;
b) receiving a transmission parameter and one or more dimensional measurement(s) of said sample body selected from the group consisting of a length measurement of the sample body, an area measurement of the sample body and a volume measurement of the sample body, where said length measurement, said area measurement and said volume measurement exclude optical path length, as inputs, wherein the dimensional measurement(s) is measured from a sample body of liquid of a shape and size encompassed by said data set and is suitable to specify a discrete body in said data set or an interpolated position intermediate to a plurality of discrete bodies in said data set, and wherein the transmission parameter is derived from the measurement of a transmission value for light through said sample body; and c) said processing apparatus determining from said data set said absorption or turbidity coefficient associated with the discrete body specified by said transmission value and said dimensional measurement(s).

23. A computer system programmed to determine an optical property selected from an absorption coefficient and a turbidity coefficient, the system comprising:

a) a memory accessible by a processor of the system, storing a set of data describing a plurality of discrete bodies of liquid of different shapes, sizes and absorption or turbidity coefficients, wherein each discrete body is captured in said data set as a combination of a measurable transmission parameter and of one or more dimensional measurements selected from lengths, areas and volumes, and wherein for each such discrete body said absorption or turbidity coefficient is indicated in said data set;

b) an interface for receiving a transmission parameter and one or more dimensional measurement(s) of said sample body selected from the group consisting of a length measurement of the sample body, an area measurement of the sample body and a volume measurement of the sample body, where said length measurement, said area measurement and said volume measurement exclude optical path length, as inputs, wherein the dimensional measurement(s) is measured from a sample body of liquid of a shape and size encompassed by said data set and is suitable to specify a discrete body in said data set or an interpolated position intermediate to a plurality of discrete bodies in said data set, and wherein the transmission parameter is derived from the measurement of a transmission value for light through said sample body; and c) the processor of the computer system being programmed to determining from said data set said absorption or turbidity coefficient associated with the discrete body specified by said transmission value and said dimensional measurement(s).

* * * * *